(12) United States Patent
Miyanaga et al.

(10) Patent No.: US 7,402,471 B2
(45) Date of Patent: *Jul. 22, 2008

(54) SEMICONDUCTOR DEVICE AND METHOD FOR MANUFACTURING THE SAME

(75) Inventors: Akiharu Miyanaga, Kanagawa (JP); Hisashi Ohtani, Kanagawa (JP); Yasuhiko Takemura, Kanagawa (JP)

(73) Assignee: Semiconductor Energy Laboratory Co., Ltd., Kanagawa-Ken (JP)

( * ) Notice: Subject to any disclaimer, the term of this patent is extended or adjusted under 35 U.S.C. 154(b) by 312 days.

This patent is subject to a terminal disclaimer.

(21) Appl. No.: 11/250,635

(22) Filed: Oct. 17, 2005

(65) Prior Publication Data

US 2006/0068569 A1 Mar. 30, 2006

Related U.S. Application Data

(60) Division of application No. 10/747,165, filed on Dec. 30, 2003, now Pat. No. 6,955,954, which is a continuation of application No. 08/975,918, filed on Nov. 21, 1997, now abandoned, which is a continuation of application No. 08/356,584, filed on Dec. 15, 1994, now abandoned.

(30) Foreign Application Priority Data

| Dec. 22, 1993 | (JP) | ................................. 05-346710 |
| Dec. 22, 1993 | (JP) | ................................. 05-346712 |
| Dec. 22, 1993 | (JP) | ................................. 05-346714 |

(51) Int. Cl.
*H01L 21/84* (2006.01)

(52) U.S. Cl. ................................ 438/166; 257/E21.134

(58) Field of Classification Search ................. 438/163, 438/166, 308; 257/E21.134
See application file for complete search history.

(56) References Cited

U.S. PATENT DOCUMENTS 3,108,914 A 10/1963 Hoerni (Continued)

FOREIGN PATENT DOCUMENTS

JP 61-063017 4/1986

(Continued)

OTHER PUBLICATIONS

R. Kakkad, J. Smith, W.S. Lau, S.J. Fonash, J. Appl. Phys. 65 (5), Mar. 1, 1989, 1989 American Institute of Physics, p. 2069-2072, "Crystallized Si Films By Low-Temperature Rapid Thermal Annealing of Amorphous Silicon".

(Continued)

*Primary Examiner*—Chandra Chaudhari
(74) *Attorney, Agent, or Firm*—Nixon Peabody LLP; Jeffrey L. Costellia

(57) ABSTRACT

A semiconductor device using a crystalline semiconductor film is manufactured. The crystalline semiconductor film is formed by providing an amorphous silicon film with a catalyst metal for promoting a crystallization thereof and then heated for performing a thermal crystallization, following which the crystallized film is further exposed to a laser light for improving the crystallinity. The concentration of the catalyst metal in the semiconductor film and the location of the region to be added with the catalyst metal are so selected in order that a desired crystallinity and a desired crystal structure such as a vertical crystal growth or lateral crystal growth can be obtained. Further, active elements and driver elements of a circuit substrate for an active matrix type liquid crystal device are formed by such semiconductor devices having a desired crystallinity and crystal structure respectively.

33 Claims, 8 Drawing Sheets

U.S. PATENT DOCUMENTS

| | | |
|---|---|---|
| 3,389,024 A | 6/1968 | Schimmer |
| 3,783,049 A | 1/1974 | Sandera |
| 3,988,762 A | 10/1976 | Cline et al. |
| 4,068,020 A | 1/1978 | Reuschel |
| 4,379,020 A | 4/1983 | Glaeser et al. |
| 4,409,724 A | 10/1983 | Tasch, Jr. et al. |
| 4,472,458 A | 9/1984 | Sirinyan et al. |
| 4,746,628 A | 5/1988 | Takafuji et al. |
| 4,911,781 A | 3/1990 | Fox et al. |
| 4,959,247 A | 9/1990 | Moser et al. |
| 5,010,033 A | 4/1991 | Tokunaga et al. |
| 5,060,197 A | 10/1991 | Park et al. |
| 5,075,259 A | 12/1991 | Moran |
| 5,130,103 A | 7/1992 | Yamagata et al. |
| 5,147,826 A | 9/1992 | Liu et al. |
| 5,236,850 A | 8/1993 | Zhang |
| 5,244,836 A | 9/1993 | Lim |
| 5,254,480 A | 10/1993 | Tran |
| 5,262,350 A | 11/1993 | Yamazaki et al. |
| 5,275,851 A | 1/1994 | Fonash et al. |
| 5,278,093 A | 1/1994 | Yonehara |
| 5,308,998 A | 5/1994 | Yamazaki et al. |
| 5,354,697 A | 10/1994 | Oostra et al. |
| 5,358,907 A | 10/1994 | Wong |
| 5,387,530 A | 2/1995 | Doyle et al. |
| 5,397,718 A | 3/1995 | Furuta et al. |
| 5,403,772 A | 4/1995 | Zhang et al. |
| 5,426,064 A | 6/1995 | Zhang et al. |
| 5,453,858 A | 9/1995 | Yamazaki |
| 5,480,811 A | 1/1996 | Chiang et al. |
| 5,481,121 A | 1/1996 | Zhang et al. |
| 5,488,000 A | 1/1996 | Zhang et al. |
| 5,492,843 A | 2/1996 | Adachi et al. |
| 5,501,989 A | 3/1996 | Takayama et al. |
| 5,508,532 A | 4/1996 | Teramoto |
| 5,508,533 A | 4/1996 | Takemura |
| 5,529,937 A | 6/1996 | Zhang et al. |
| 5,531,182 A | 7/1996 | Yonehara |
| 5,534,716 A | 7/1996 | Takemura |
| 5,534,884 A | 7/1996 | Mase et al. |
| 5,543,352 A | 8/1996 | Ohtani et al. |
| 5,563,426 A | 10/1996 | Zhang et al. |
| 5,569,610 A | 10/1996 | Zhang et al. |
| 5,569,936 A | 10/1996 | Zhang et al. |
| 5,580,792 A | 12/1996 | Zhang et al. |
| 5,585,291 A | 12/1996 | Ohtani et al. |
| 5,589,694 A | 12/1996 | Takayama et al. |
| 5,595,923 A | 1/1997 | Zhang et al. |
| 5,595,944 A | 1/1997 | Zhang et al. |
| 5,604,360 A | 2/1997 | Zhang et al. |
| 5,605,846 A | 2/1997 | Ohtani et al. |
| 5,606,179 A | 2/1997 | Yamazaki et al. |
| 5,608,232 A | 3/1997 | Yamazaki et al. |
| 5,612,250 A | 3/1997 | Ohtani et al. |
| 5,614,426 A | 3/1997 | Funada et al. |
| 5,614,733 A | 3/1997 | Zhang et al. |
| 5,616,506 A | 4/1997 | Takemura |
| 5,620,910 A | 4/1997 | Teramoto |
| 5,621,224 A | 4/1997 | Yamazaki et al. |
| 5,624,851 A | 4/1997 | Takayama et al. |
| 5,637,515 A | 6/1997 | Takemura |
| 5,639,698 A | 6/1997 | Yamazaki et al. |
| 5,643,826 A | 7/1997 | Ohtani et al. |
| 5,646,424 A | 7/1997 | Zhang et al. |
| 5,650,338 A | 7/1997 | Yamazaki et al. |
| 5,654,203 A | 8/1997 | Ohtani et al. |
| 5,656,825 A | 8/1997 | Kusumoto et al. |
| 5,663,077 A | 9/1997 | Adachi et al. |
| 5,677,549 A | 10/1997 | Takayama et al. |
| 5,696,003 A | 12/1997 | Makita et al. |
| 5,696,386 A | 12/1997 | Yamazaki |
| 5,696,388 A | 12/1997 | Funada et al. |
| 5,700,333 A | 12/1997 | Yamazaki et al. |
| 5,705,829 A | 1/1998 | Miyanaga et al. |
| 5,712,191 A | 1/1998 | Nakajima et al. |
| 5,744,824 A | 4/1998 | Kousai et al. |
| 5,773,327 A | 6/1998 | Yamazaki et al. |
| 5,773,846 A | 6/1998 | Zhang et al. |
| 5,818,076 A | 10/1998 | Zhang et al. |
| 5,879,977 A | 3/1999 | Zhang et al. |
| 5,882,960 A | 3/1999 | Zhang et al. |
| 5,897,347 A | 4/1999 | Yamazaki et al. |
| 5,913,112 A | 6/1999 | Yamazaki et al. |
| 5,923,962 A | 7/1999 | Ohtani et al. |
| 5,942,768 A | 8/1999 | Zhang |
| 5,956,579 A | 9/1999 | Yamazaki et al. |
| 5,962,870 A | 10/1999 | Yamazaki et al. |
| 5,985,704 A | 11/1999 | Adachi et al. |
| 6,037,610 A | 3/2000 | Zhang et al. |
| 6,048,780 A | 4/2000 | Hayakawa |
| 6,060,725 A | 5/2000 | Zhang et al. |
| 6,110,770 A | 8/2000 | Zhang et al. |
| 6,140,165 A | 10/2000 | Zhang et al. |
| 6,171,890 B1 | 1/2001 | Adachi et al. |
| 6,211,536 B1 | 4/2001 | Zhang |
| 6,261,875 B1 | 7/2001 | Zhang et al. |
| 6,285,042 B1 | 9/2001 | Ohtani et al. |
| 6,331,723 B1 | 12/2001 | Yamazaki et al. |
| 6,335,541 B1 | 1/2002 | Ohtani et al. |
| 6,348,367 B1 | 2/2002 | Ohtani et al. |
| 6,413,805 B1 | 7/2002 | Zhang et al. |
| 6,451,638 B1 | 9/2002 | Zhang et al. |
| 6,541,313 B2 | 4/2003 | Zhang et al. |
| 6,599,359 B2 | 7/2003 | Adachi et al. |
| 6,608,325 B1 | 8/2003 | Zhang et al. |
| 6,624,445 B2 | 9/2003 | Miyanaga et al. |
| 6,627,487 B2 | 9/2003 | Zhang |
| 6,730,549 B1 | 5/2004 | Zhang et al. |
| 6,756,657 B1 | 6/2004 | Zhang et al. |
| 6,798,023 B1 | 9/2004 | Ohtani et al. |
| 6,939,749 B2 | 9/2005 | Zhang et al. |
| 6,955,954 B2 | 10/2005 | Miyanaga et al. |
| 6,987,283 B2 | 1/2006 | Zhang et al. |
| 6,998,639 B2 | 2/2006 | Ohtani et al. |
| 7,148,094 B2 | 12/2006 | Zhang et al. |
| 2002/0024047 A1 | 2/2002 | Yamazaki et al. |

FOREIGN PATENT DOCUMENTS

| | | |
|---|---|---|
| JP | 64-045162 | 2/1989 |
| JP | 01-206632 | 8/1989 |
| JP | 02-119122 | 5/1990 |
| JP | 02-140915 | 5/1990 |
| JP | 03-280420 | 12/1991 |
| JP | 05-009090 | 1/1993 |
| JP | 05-114724 | 5/1993 |
| JP | 05-203991 | 8/1993 |
| JP | 05-210364 | 8/1993 |
| JP | 07-176479 | 7/1994 |
| JP | 06-267988 | 9/1994 |
| JP | 06-268212 | 9/1994 |
| JP | 06-318700 | 11/1994 |
| JP | 06-333824 | 12/1994 |
| JP | 06-333825 | 12/1994 |
| JP | 06-349735 | 12/1994 |
| JP | 07-058338 | 3/1995 |
| JP | 07-161634 | 6/1995 |
| JP | 07-235492 | 9/1995 |
| JP | 07-335548 | 12/1995 |
| JP | 08-017741 | 1/1996 |

OTHER PUBLICATIONS

G. Liu, S.J. Fonash, Appl. Phys. Lett. 62 (20), May 17, 1993, 1993 American Institute of Physics, p. 2554-2556, "Polycrystalline Silicon Thin Film Transistors on Corning 7059 Glass substrates Using Short Time, Low Temperature Processing".

G. Liu and S.J. Fonash, Appl. Phys. Lett. 55 (7), Aug. 14, 1989, 1989 American Institute of Physics, p. 660-662, "Selective Area Crystallization of Amorphous Silicon Films by Low-Temperature Rapid Thermal Annealing".

R. Kakkad, G. Liu, S.J. Fonash, Journal of Non-Crystalline Solids, vol. 115, (1989), p. 66-68, "Low Temperature Selective Crystallization of Amorphous Silicon".

S. Caune et al., Appl. Surf. Sci., 36 (1989), "Combined CW laser and furnace annealing of a-Si and Ge in contact with some metals", pp. 597-604.

C. Hayzelden et al., "*In Situ* Transmission Electron Microscopy Studies of Silicide-Mediated Crystallization of Amorphous Silicon" (3 pages).

S. P. Murarka, "Silicides for VLSI Applications", p. 112, 82, no date.

T. Hempel et al., Solid State Communications, vol. 85, No. 11 (1993) pp. 921-924 "Needle-Like Crystallization of Ni Doped Amorphous Silicon Thin Films".

F. Spaepen et al., Crucial Issues in Semic. Mater. & Proc. Technol., S. Coffa et al. (eds)., Kulwer (1992) 483-99.

T.B. Suresh et al., Thin Solid Films, 252 (1994) "Electroless Plated Ni Contacts to a-Si:H", pp. 78-81.

F. Oki et al., Japan Journal Appl. Phys., 8 (1969) 1056, "Effect of deposited metals on the crystallization temperature . . . ".

A. V. Dvurechenskii et al., Phys. Stat. Sol. (a) 95 (1986) pp. 635-640 "Transport Phenomena in Amorphous Silicon Doped by Ion Implantation of 3d Metals".

J. Stoemenos et al., Appl. Phys. Lett., vol. 58, No. 11, Mar. 18, 1991, pp. 1196-1198 "Crystallization of Amorphous Silicon by Reconstructive Transformation Utilizing Gold".

C. Hayzelden et al., J. Appl. Phys., vol. 73, No. 12, Jun. 15, 1993, pp. 8279-8289, Silicide Formation and Silicide- Mediated Crystallization ofNickel-Implanted Amorphous Silicon Thin Films.

A. Yu. Kuznetsov et al., Nucl. Instr. & Meth. Phys. Res. B80/81 (1993) pp. 990-993, "Enhanced Solid Phase Epitaxial Recrystallization of Amorphous Silicon Due to Nickel Silicide Precipitation Resulting From Ion Implantation and Annealing".

Y. Kawazu et al., Japanese Journal of Applied Physics, vol. 29, No. 4, Apr. 1990, pp. 729-738, "Initial Stage of the Interfacial Reaction between Nickel and Hydrogenated Amorphous Silicon".

SEMICONDUCTOR DEVICE AND METHOD FOR MANUFACTURING THE SAME

FIELD OF THE INVENTION

The present invention relates to an active-matrix type liquid crystal device or thin film integrated circuit devices using a semiconductor layer with crystallinity.

BACKGROUND OF THE INVENTION

Active-matrix type liquid crystal devices have been well known which utilize thin film transistors (generally called as TFT). In a conventional active-matrix liquid crystal display device, a peripheral circuit member is constituted by IC and is externally connected to terminals of matrix wirings of the pixels. Further, it is also known to form TFTs for forming a peripheral circuit on the same substrate on which TFTs are arranged in a matrix as a switching element in a pixel region.

Since the TFTs formed on a peripheral circuit portion are to drive the TFTs formed in a matrix form on a pixel portion, they are required to have a capability of passing a large amount of electric current therethrough. Specifically, they are required to have a large ON current and a large mobility.

On the other hand, the TFTs formed on the pixel portion are not required to have a large mobility. Rather, they need to have a lower OFF current (leak current) in order to maintain electric charges on pixel electrodes. Accordingly, the required characteristics for the TFTs of a peripheral circuit are different from those for the TFTs of a pixel portion.

Further, an amorphous silicon film has been used to form a TFT but its characteristics are not satisfactory. Therefore, a TFT using a crystalline silicon film has been investigated. Generally, it is necessary to perform a thermal annealing at 600° C. or higher and for more than 24 hours for obtain a crystalline silicon film from an amorphous silicon film. However, a glass substrate which is usually used as a substrate of a liquid crystal device can not endure such a thermal annealing because for example, a Corning 7059 glass has a distortion point of 593° C. In particular, one problem is that the glass substrate tends to be distorted because of the high temperature so that it is difficult to increase the size of the substrate.

The inventors of the present application have confirmed through their experiments that by contacting a slight amount of catalyst metal such as nickel or platinum with an amorphous silicon film, it is possible to crystallize the silicon film at lower temperatures, for example, at 550° C. for about 4 hours. And the resultant crystallinity is comparable with that obtained the above conventional thermal treatment at 600° C. The inventors considered that these metal functions as a catalyst to promote the crystallization of an amorphous silicon film.

The inventors also confirmed that there are two types of crystallization in the case of using a catalyst as indicated below.

(1) A crystallization proceeds in a direction normal to a substrate in a region where a catalyst was introduced.

(2) A crystallization proceeds in a direction parallel with a substrate from a region to which a catalyst was introduced toward a region to which a catalyst was not introduced.

The crystal structure in the case of (2) was confirmed by using a TEM (transmission type electron microscope) that columnar crystals grow in a direction parallel with a substrate. Also, the amount of nickel necessary for causing the above first type of crystallization is different from the amount of nickel necessary for causing the above second type of crystallization. For example, when the (2) type of crystallization extends about 30 μm, the amount of the nickel necessary to be introduced thereto is 10 times as much as that required in the case of (1).

In the present specification, hereinbelow, the region where the above (1) type of crystallization occurs will be called as a vertical growth region and the region where the above (2) type of crystallization occurs will be called as a lateral growth region.

SUMMARY OF THE INVENTION

It is an object of the present invention to form thin film transistors on a pixel region (pixel TFTs) and thin film transistors on a peripheral circuit region on a same substrate through a simple process for an active-matrix type liquid crystal device.

Moreover, it is another object of the present invention that, in an active-matrix type liquid crystal device, pixel TFTs have a different crystallinity than TFTs formed on a peripheral circuit region.

In accordance with one aspect of the present invention, the method of the present invention includes a step of irradiating a laser light or a light having a sufficient strength on a selected portion of a semiconductor film to constitute a peripheral circuit region.

In accordance with another aspect of the invention, TFTs constituting a peripheral circuit are formed with a crystalline silicon film in which crystals grew in a direction approximately parallel with a direction along which carriers of the TFTs flow while pixel TFTs are formed with a crystalline silicon film in which crystals grew in a direction approximately perpendicularly with respect to a carrier direction of the pixel TFTs. The carrier direction means the direction along source and drain regions of the TFT. Namely, when a carrier direction is approximately aligned with a crystal growth direction, since carriers move along the direction of grain boundaries, the influence of the grain boundaries with respect to the carrier flow is suppressed and thus such a TFT can have a higher mobility. Accordingly, such a TFT is suitable for forming a peripheral circuit which requires a higher ON current. On the other hand, when a carrier direction is perpendicular to a crystal growth direction, since carriers have to cross grain boundaries, the OFF current can be decreased while the ON current is decreased. Accordingly, such a TFT is suitable as a pixel TFT for switching a pixel electrode in an electro-optical device.

It is still a further aspect of the present invention that TFTs having a channel region formed with a vertical growth silicon film (i.e. in which crystals grew perpendicularly to the substrate) and TFTs having a channel region formed with a lateral growth silicon (i.e. in which crystals grew horizontally with the substrate) are both formed on the same substrate. Specifically, the TFTs associated with the vertical growth region is suitable as pixel TFTs for switching pixel electrodes while the TFTs associated with the lateral growth region is suitable as a peripheral circuit for driving the pixel TFTs. This feature is based on the inventors' discovery that the amount of a catalyst required for forming a vertical growth film and that for forming a lateral growth film are different from each other. In order to accurately control the amount of a catalyst to be introduced into a semiconductor film, the inventors utilize a liquid for carrying a catalyst therein.

In accordance with the present invention the catalyst may be one or more elements selected from the group consisting of Ni, Pd, Pt, Cu, Ag, Au, In, Sn, P, As and Sb. Alternatively, the catalyst may be one or more elements selected from the group consisting of Group VIII elements, Group IIIb elements, Group IVb elements and Group Vb elements.

BRIEF DESCRIPTION OF THE DRAWINGS

The foregoing and other objects and features of the present invention will be explained in detail with reference to the attached drawings in which.

DETAILED DESCRIPTION OF THE PREFERRED EMBODIMENTS OF THE INVENTION

Figure 1:
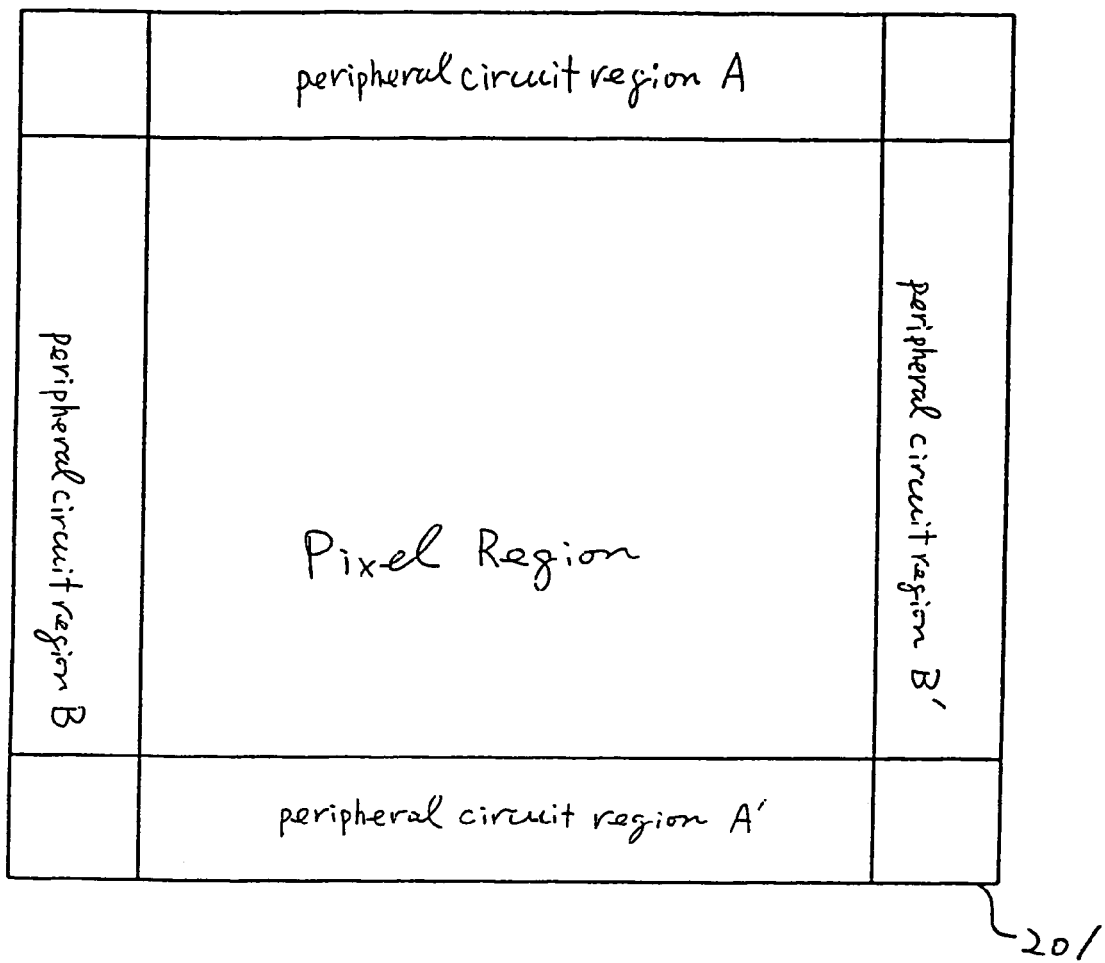
FIG. 1 shows a schematic diagram of an active-matrix type liquid crystal device in accordance with the present invention.

FIG. 1 shows a schematic diagram of a circuit substrate of an active matrix type liquid crystal device in accordance with the present invention.

In FIG. 1, on a substrate 201, there are peripheral circuit regions (A) and (B), redundant peripheral circuit regions (A') and (B') which are used in case where the circuits (A) and (B) are defective. There is also a pixel region having a plurality of pixel TFTs arranged in a matrix form on the same substrate for switching a plurality of pixel electrodes.

In accordance with the preferred embodiments of the invention, a catalyst for promoting the crystallization of a semiconductor film is introduced by a method in which a liquid carrying the catalyst therein is used as explained below.

For preparing a liquid carrying the catalyst, it is possible to use a polar solvent selected from the group consisting of water, alcohol, acid and ammonium. Examples of nickel compounds which can be dissolved in a polar solvent are nickel bromide, nickel acetate, nickel oxalate, nickel carbonate, nickel chloride, nickel iodide, nickel nitrate, nickel sulfate, nickel formate, nickel acetylacetonate, 4-cyclohexyl butyric acid, nickel oxide and nickel hydroxide.

Also, it is possible to use a non-polar solvent for dissolving a nickel compound, for example, benzene, toluene, xylene, carbon tetrachloride, chloroform or ether. Examples of nickel compounds suitable for such a solvent are nickel acetyl acetonate and 2-ethyl hexanoic acid nickel.

Also, it is advantageous to add a surface activation agent to a catalyst containing solution in order to improve the adhesivity of the catalyst to the surface and control the adsorption property. The surface activation agent may be applied directly onto the surface before coating the solution.

In the above mentioned solutions, nickel which is a catalyst element is completely dissolved in the solution. However, it is to be understood that nickel may not be completely dissolved in a solution. For example, it is possible to use a material like an emulsion in which nickel metal or nickel compound powders are uniformly dispersed. It is also possible to use a solution which is for forming a silicon oxide film, for example, OCD (Ohka Diffusion Source) which is supplied by Tokyo Ohka Industry. In such a case it is possible to form a silicon oxide film which contains a catalyst therein by simply coating the solution and then baking at 200° C. Desired impurities can be also added to the solution.

The foregoing solutions are initially formed on an amorphous silicon film by a spin coating method and then dried so that a film containing a catalyst for promoting a crystallization of the silicon film is formed.

EXAMPLE 1

This example relates to a manufacture of a circuit substrate of an active matrix liquid crystal device as shown in FIG. 1 in accordance with the above mentioned first aspect of the present invention.

Figure 2A:
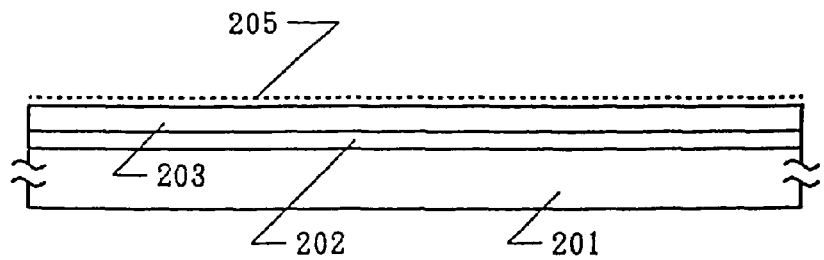
FIGS. 2A-2F show a manufacturing method of a thin film transistor for a peripheral circuit in accordance with Example 1 of the present invention.

FIGS. 2A-2F are cross sectional views for showing a manufacturing method of a TFT in the peripheral circuit regions of FIG. 1. On the other hand, FIGS. 3A-3F are cross sectional views for showing a manufacturing method of a TFT in the pixel region of FIG. 1. Therefore, FIGS. 2A-2F and FIGS. 3A-3F correspond with each other and the both TFTs are formed on the same substrate. It is to be understood that each step of FIGS. 2A-2F and FIGS. 3A-3F is carried out simultaneously. For example, the step of FIG. 2A is simultaneously performed as the step of FIG. 3A. Also, the same reference number is used for showing a like element.

Figure 3A:
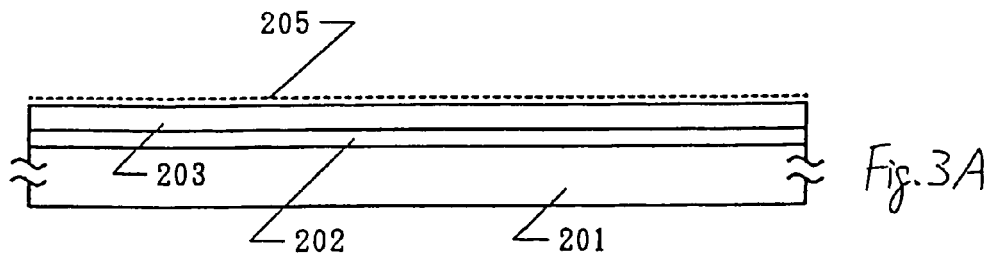
FIGS. 3A-3F show a manufacturing method of a thin film transistor for a pixel region in accordance with Example 1 of the present invention.
Figure 3B:
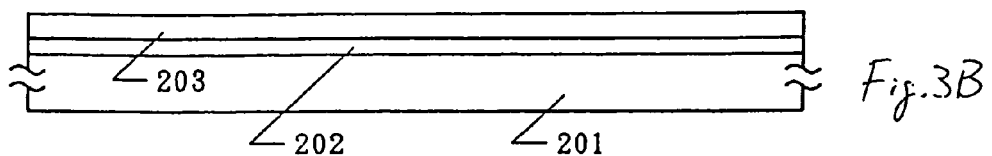

Initially, referring to FIGS. 2A and 3A, the substrate 201 is cleaned by washing, following which a silicon oxide film 202 of 2000 Å thick is formed as a base layer by a plasma CVD using TEOS (tetra-ethoxy-silane) and oxygen as starting materials.

Then, an amorphous silicon film 203 of an intrinsic type is formed by plasma CVD to a thickness of 500-1500 Å, for example, 1000 Å. On the amorphous silicon film 203, a solution containing nickel as a catalyst, for example, a nickel acetate solution is formed by coating. The concentration of nickel in the solution is 10 ppm. Also, it is advantageous to form a very thin oxide film on the amorphous silicon film before the formation of the nickel containing solution in order to improve the wettability of the surface. The thickness of the oxide film should be several tens angstroms in order that nickel can penetrate through it.

It should be noted that a plasma treatment, evaporation, sputtering or CVD may be used to form a nickel film or nickel containing film instead of the above coating method.

After drying the coated solution 205, the silicon film 203 is crystallized by a thermal annealing at a temperature of 500-620° C., for example, 550° C., for a period of 4 hours in a nitrogen atmosphere. During the annealing, nickel diffuses into the silicon film from the surface and promotes the crystallization. The crystallization proceeds in a direction perpendicular to the substrate.

Figure 2B:
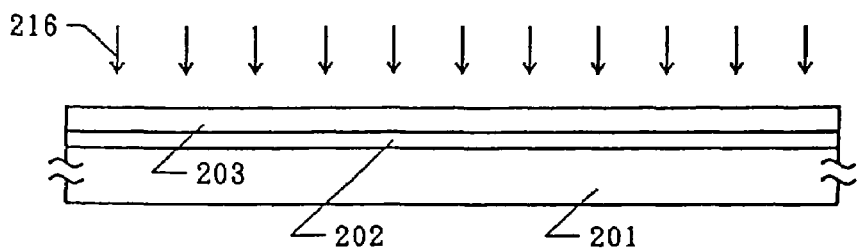

Referring to FIG. 2B, after the above crystallization, only the region of the semiconductor film which corresponds to the peripheral circuit region is irradiated with a laser light 216 in order to improve the crystallinity. As a laser light, a KrF excimer laser (wavelength 248 nm, pulse width 20 nsec) is used with an energy density of 250 mJ/cm$^2$ and at 2 shots/site.

It is desirable to heat the substrate by another energy source to 400° C. during the laser irradiation in order to increase the effect of the laser irradiation.

Also, other known lasers may be used instead of the excimer laser. Moreover, it is also possible to use an intense light instead of laser. For example, an infrared light of a wavelength of 1.2 μm may be used. The effect of the IR light irradiation is comparable with the effect obtainable with a heat annealing at a high temperature for several minutes.

Figure 2C:
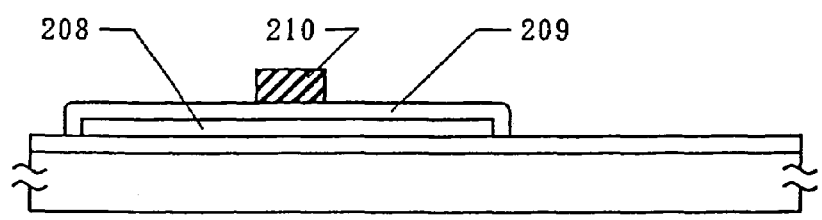
Figure 3C:
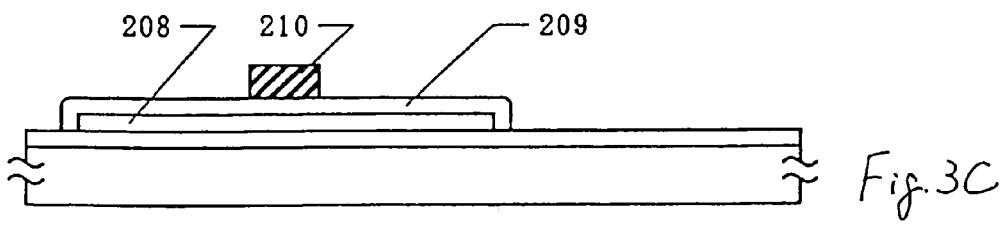

The concentration of nickel in the silicon film after the crystallization is about $10^{18}$ atoms/cm$^3$. Then, the silicon film 203 is patterned by dry etching to form active regions 208 in an island form as shown in FIGS. 2C and 3C.

Thereafter, the surface of the active regions 208 is exposed to a 100 volume % water vapor at a pressure of 10 atm and at a temperature of 500-600° C., typically, 550° C. for 1 hour in order to oxidize the surface and form a silicon oxide film 209. The thickness of the silicon oxide film 209 is 1000 Å. After the oxidation, the substrate is then exposed to an ammonium atmosphere (1 atm, 100%) at 400° C. At this condition, an infrared light having a peak at a wavelength of 0.6-4 μm, for example, 0.8-1.4 μm for 30-180 seconds is irradiated onto the silicon oxide film 209 to perform a nitridation. It is possible to add HCl at 0.1-10% to the atmosphere during this nitridation.

Subsequently, an aluminum film containing scandium at 0.01-0.2% is formed by sputtering to a thickness of 3000-8000 Å, e.g. 6000 Å and then patterned into a gate electrode 210.

Figure 2D:
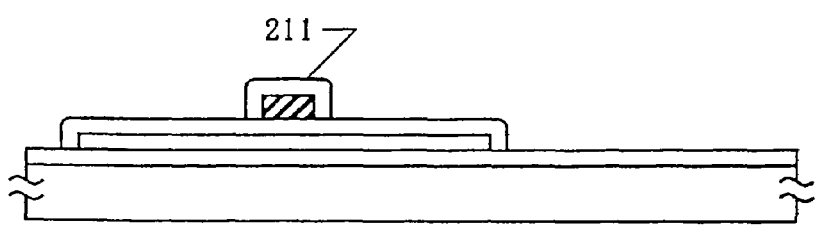
Figure 3D:
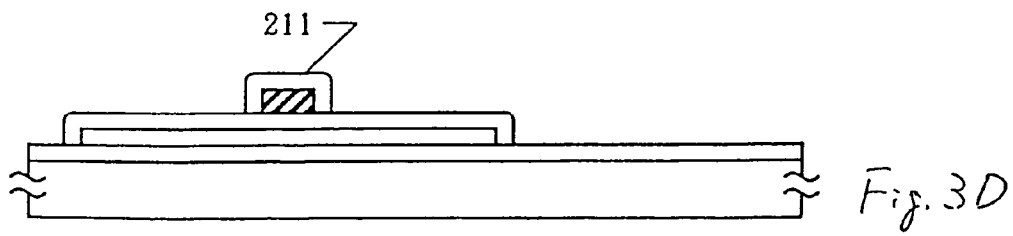

Then, referring to FIGS. 2D and 3D, the surface of the aluminum gate electrode is anodic oxidized to form an anodic oxide layer 211 of a thickness of 2000 Å. The anodic oxidation is carried out within an ethylene glycol solution in which a tartaric acid is contained at 1-5%. The thickness of the anodic oxide layer 211 will determine the thickness of the offset gate area in the later step.

Figure 2E:
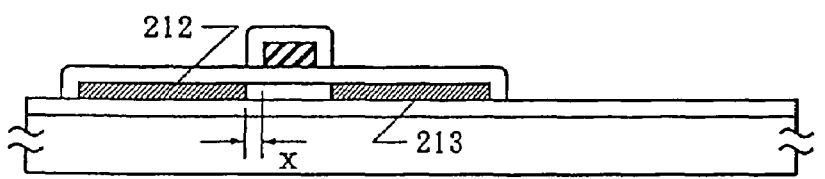
Figure 3E:
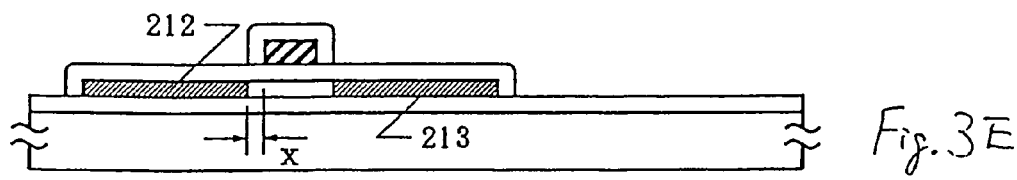

Referring then to FIGS. 2E and 3E, using the gate electrode 210 and the surrounding anodic oxide film 211 as a mask, an N-type conductivity impurity (phosphorous, here) is introduced into the active layer in a self-aligning manner by ion doping method (also called as plasma doping method) in order to form impurity regions 212 and 213. Phosphine (PH$_3$) is used as a dopant gas. The acceleration voltage is 60-90 kV, for example, 80 kV. The dose amount is $1 \times 10^{15}$-$8 \times 10^{15}$ cm$^{-2}$, for example, $4 \times 10^{15}$ cm$^{-2}$. As can be seen in the drawing, the impurity regions 212 and 213 are offset from the gate electrode by a distance "x". This configuration is advantageous for reducing a leak current (off current) which occurs when applying a reverse bias voltage (i.e. a negative voltage in the case of an NTFT) to the gate electrode. In particular, since it is desired that electric charges stored in a pixel electrode be maintained without leaking in order to obtain an excellent display, the offset configuration is particularly advantageous when the TFT is used for controlling a pixel of an active matrix.

Thereafter, an annealing is performed with a laser irradiation. As a laser, a KrF excimer laser (wavelength: 248 nm, pulse width: 20 nsec.) or other lasers may be used. The conditions of the laser irradiation in the case of KrF excimer laser are: energy density is 200-400 mJ/cm$^2$, for example, 250 mJ/cm$^2$, a number of shots is 2-10 shots per one site, for example, 2 shots. Preferably, the substrate is heated to 200-450° C. to enhance the effect of the irradiation.

Figure 2F:
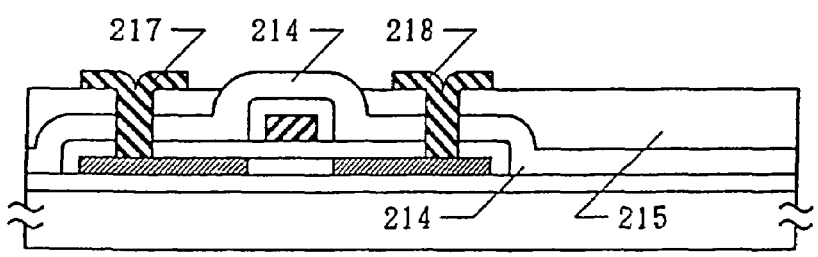
Figure 3F:
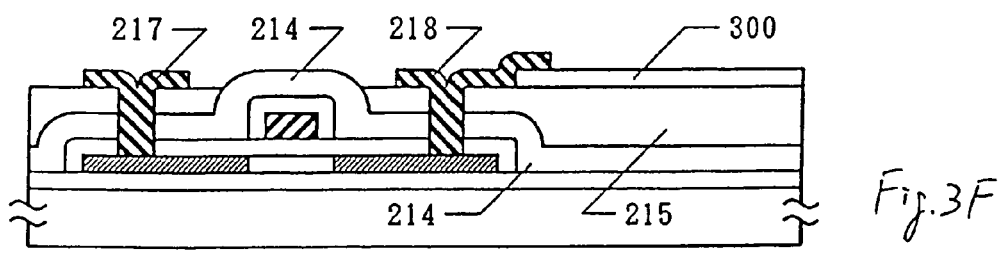

Referring to FIGS. 2F and 3F, an interlayer insulating film 214 of silicon oxide is formed through a plasma CVD to a thickness of 6000 Å. Further, a transparent polyimide film 215 is formed by spin coating to obtain a leveled surface. Then, in the pixel region, a transparent conductive film made of, for example, indium tin oxide is formed on the leveled surface and patterned into a pixel electrode 300 as shown in FIG. 3F. The ITO electrode will be connected to a terminal of a TFT as a pixel electrode.

Then, the interlayer insulating films 214 and 215 are provided with contact holes, through which electrode/wirings 217 and 218 are formed to contact the impurity regions of the TFT. The electrode/wirings 217 and 218 are formed of a metallic material, for example, a multi-layer of titanium nitride and aluminum. As shown in FIG. 3F, one electrode 218 of the pixel TFT is connected to the pixel electrode 300 made of ITO.

Finally, an annealing in a hydrogen atmosphere of 1 atm is carried out at 350° C. for 30 minutes in order to complete a pixel circuit of an active matrix circuit having TFTs.

EXAMPLE 2

The present example relates to the second aspect of the present invention as mentioned before. Specifically, this example is directed to a manufacture of a circuit substrate for an electro-optical device of the same type shown in FIG. 1. In particular, the TFTs for both the peripheral circuit and the pixel circuit have their semiconductor layer in which crystals extend (grow) in a direction parallel with the substrate surface.

FIGS. 4A-4F are cross sectional views for showing a manufacturing method of a TFT in peripheral circuit regions of FIG. 1 in accordance with the present example, while FIGS. 5A-5F are cross sectional views for showing a manufacturing method of a TFT in the pixel region of FIG. 1 in accordance with the present example. Therefore, FIGS. 4A-4F and FIGS. 5A-5F correspond with each other and the both TFTs are formed on the same substrate. Also, the same reference number is used for showing a like element.

Figure 4A:
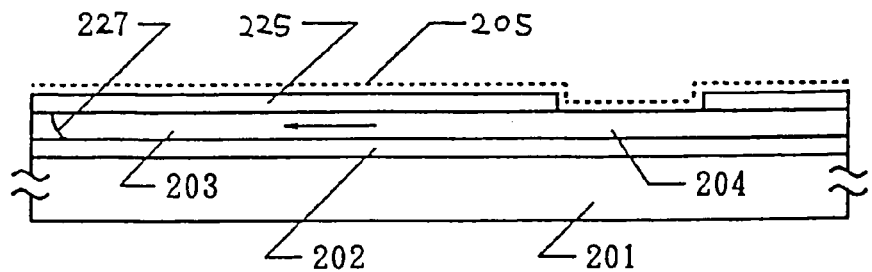
FIGS. 4A-4F show a manufacturing method of a thin film transistor for a peripheral circuit in accordance with Example 2 of the present invention.
Figure 5A:
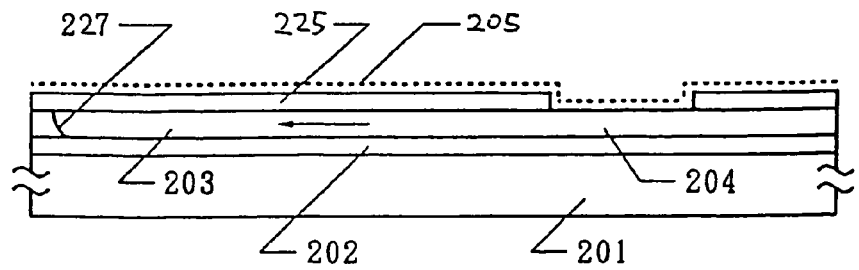
FIGS. 5A-5F show a manufacturing method of a thin film transistor for a pixel region in accordance with Example 2 of the present invention.
Figure 5B:
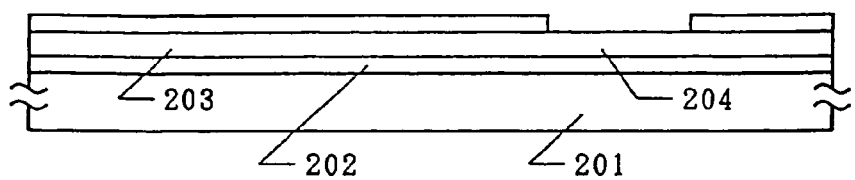

Initially, referring to FIGS. 4A and 5A, the substrate 201 is cleaned by washing, following which a silicon oxide film 202 of 2000 Å thick is formed as a base layer by a plasma CVD using TEOS (tetra-ethoxy-silane) and oxygen as starting materials.

Then, an amorphous silicon film 203 of an intrinsic type is formed by plasma CVD to a thickness of 500-1500 Å, for example, 1000 Å. Subsequently, a silicon oxide film 225 of 500-2000 Å thick, for example, 1000 Å is formed by plasma CVD. Then, the silicon oxide film 225 is partly etched to form an exposed region 204 of the amorphous silicon film, which is to be provided with nickel in the later step.

Then, a solution containing nickel as a catalyst, for example, a nickel acetate solution is formed by coating. The concentration of nickel in the solution is 100 ppm. Also, it is advantageous to form a very thin oxide film on the amorphous silicon film before the formation of the nickel containing solution in order to improve the wettability of the surface. The thickness of the oxide film should be several tens angstroms or less in order that nickel can penetrate through it.

It should be noted that a plasma treatment, evaporation, sputtering or CVD may be used to form a nickel film or nickel containing film instead of the above coating method.

After drying the coated solution 205, the silicon film 203 is crystallized by thermal annealing at a temperature of 500-620° C., for example, 550° C., for 4 hours in a nitrogen atmosphere. The crystallization starts at the region 204 of the silicon film to which nickel is directly introduced and it proceeds to adjacent regions in a direction parallel with the substrate surface as shown by an arrow in the figure. Accordingly, there is formed a crystalline silicon film in which crystals grow parallel with the substrate below the silicon oxide film 225. The length of the lateral growth region is about 25 µm. Also, the direction of the crystal growth in the lateral growth region is approximately aligned with the <111> axis of the crystal.

Figure 4B:
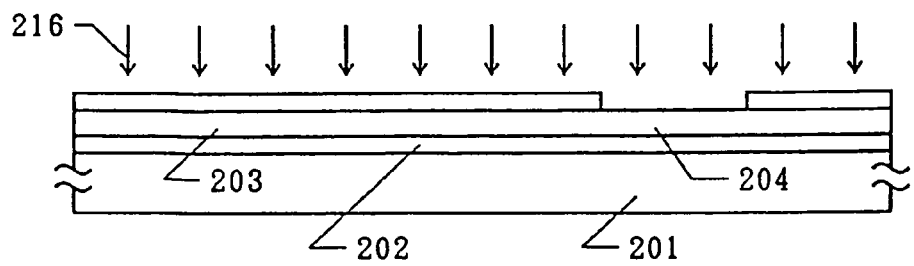

Referring to FIG. 4B, after the above crystallization, the semiconductor film only in the peripheral circuit region is irradiated with a laser light 216 in order to improve the crystallinity thereof. As a laser light, a KrF excimer laser (wavelength 248 nm, pulse width 20 nsec) is used with an energy density of 250 mJ/cm$^2$ and at 2 shots/site. It is desirable to heat the substrate by another energy source to 400° C. during the laser irradiation in order to increase the effect of the laser irradiation.

Also, another kind of laser may be used instead of an excimer laser. Moreover, it is possible to use an intense light instead of laser. For example, an infrared light of a wavelength of 1.2 µm may be used.

Then, the silicon oxide film 205 is removed by etching. At the same time, the thin oxide film formed on the region 204 is also removed. Further, the silicon film 203 is patterned by dry etching in order to form active regions 208 in the form of islands. The region 204 was directly introduced with nickel so that the concentration of the nickel in this region is higher. Also, the end portion 227 of crystal growth contains nickel at a higher concentration. On the other hand, the region 204 contains nickel at a lower concentration than the regions 204 and 227. Accordingly, the patterning of the silicon film is performed in such a manner that the silicon island 208 (active region) does not overlap with the high concentration regions 204 or 227.

Figure 4C:
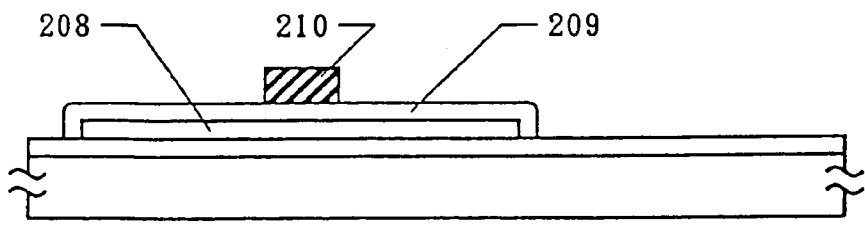
Figure 5C:
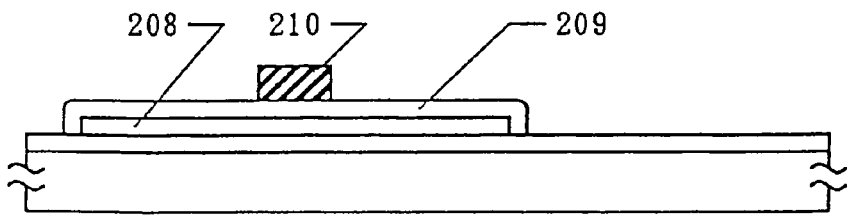

Thereafter, the surface of the active regions 208 is exposed to a 100 volume % water vapor at a pressure of 10 atm and at a temperature of 500-600° C., typically, 550° C. for 1 hour in order to oxidize the surface and form a silicon oxide film 209 as shown in FIGS. 4C and 5C. The thickness of the silicon oxide film 209 is 1000 Å. After the oxidation, the substrate is exposed to an ammonium atmosphere (1 atm, 100%) at 400° C. At this condition, an infrared light having a peak at a wavelength of 0.6-4 µm, for example, 0.8-1.4 µm for 30-180 seconds is irradiated onto the silicon oxide film 209 to perform a nitridation. HCl may be added at 0.1-10% to the atmosphere during this nitridation.

Subsequently, an aluminum film containing scandium at 0.01-0.2% is formed by sputtering to a thickness of 3000-8000 Å, for example, 6000 Å and then patterned into a gate electrode 210.

Figure 4D:
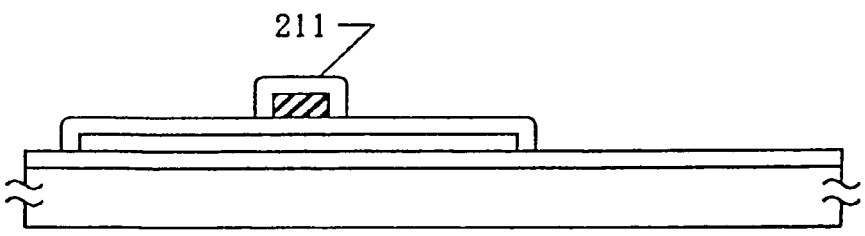
Figure 5D:
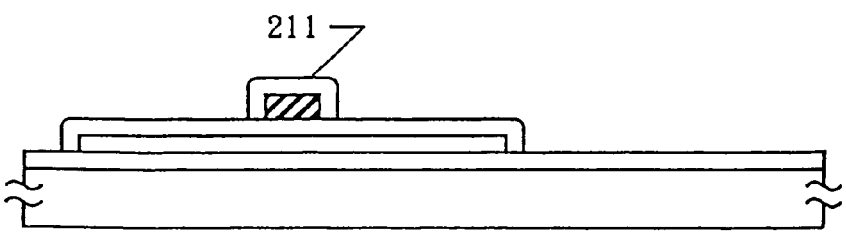

Then, referring to FIGS. 4D and 5D, the surface of the aluminum gate electrode is anodic oxidized to form an anodic oxide layer 211 of a thickness of 2000 Å. The anodic oxidation is carried out within an ethylene glycol solution in which a tartaric acid is contained at 1-5%. The thickness of the anodic oxide layer 211 will determine the thickness of the offset gate area in the subsequent impurity introducing step by ion doping.

Figure 4E:
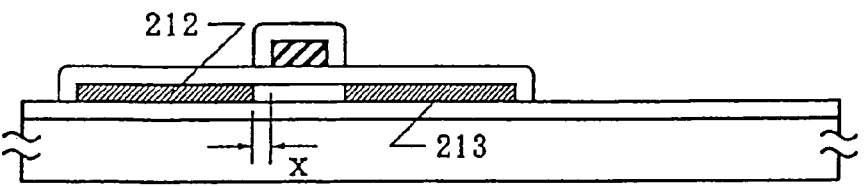
Figure 5E:
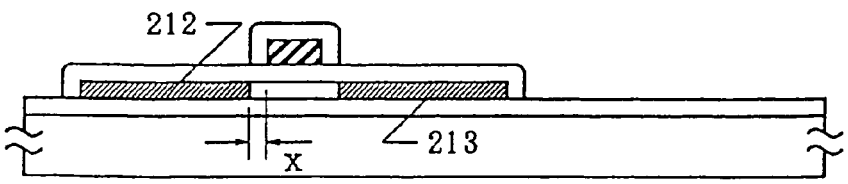

Referring then to FIGS. 4E and 5E, using the gate electrode 210 and the surrounding anodic oxide film 211 as a mask, an N-type conductivity impurity (phosphorous, here) is introduced into the active layer in a self-aligning manner by ion doping method (also called as plasma doping method) in order to form impurity regions 212 and 213 as source and drain regions. Phosphine (PH$_3$) is used as a dopant gas. The acceleration voltage is 60-90 kV, for example, 80 kV. The dose amount is 1×10$^{15}$-8×10$^{15}$ cm$^{-2}$, for example, 4×10$^{15}$ cm$^{-2}$. As can be seen in the drawing, the impurity regions 212 and 213 are offset from the gate electrode by a distance "x". This configuration is advantageous for reducing a leak current (off current) which occurs when applying a reverse bias voltage (i.e. a negative voltage in the case of an NTFT) to the gate electrode. In particular, since it is desired that electric charges stored in a pixel electrode be maintained without leaking in order to obtain an excellent display, the offset configuration is particularly advantageous when the TFT is used for controlling a pixel of an active matrix.

Thereafter, an annealing is performed with a laser irradiation. As a laser, a KrF excimer laser (wavelength: 248 nm, pulse width: 20 nsec.) or other lasers may be used. The conditions of the laser irradiation in the case of KrF excimer laser are: energy density is 200-400 mJ/cm$^2$, for example, 250 mJ/cm$^2$, a number of shots is 2-10 shots per one site, for example, 2 shots. Preferably, the substrate is heated to 200-450° C. to enhance the effect of the irradiation.

Figure 4F:
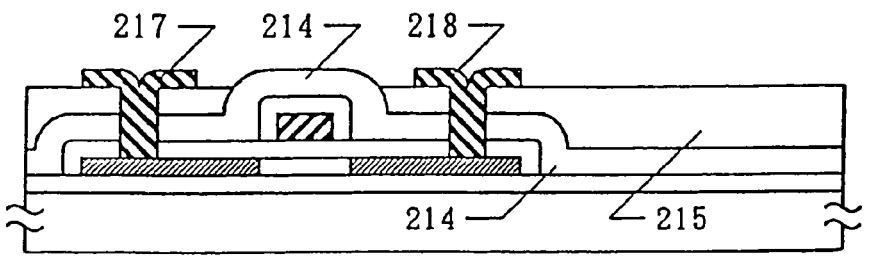
Figure 5F:
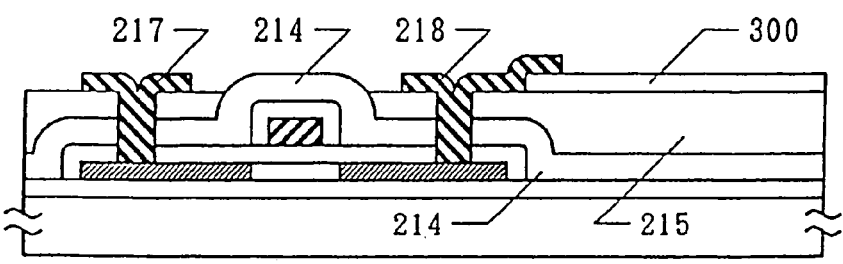

Referring to FIGS. 4F and 5F, an interlayer insulating film 214 of silicon oxide is formed through a plasma CVD to a thickness of 6000 Å. Further, a transparent polyimide film 215 is formed by spin coating to obtain a leveled surface. Then, a transparent conductive film made of, for example, indium tin oxide is formed on the leveled surface and patterned into a pixel electrode 300 as shown in FIG. 5F. The ITO electrode will be connected to a terminal of a TFT as a pixel electrode in the pixel region.

Then, the interlayer insulating films 214 and 215 are provided with contact holes, through which electrode/wirings 217 and 218 are formed to contact the impurity regions of the TFT. The electrode/wirings 217 and 218 are formed of a metallic material, for example, a multi-layer of titanium nitride and aluminum. As shown in FIG. 5F, one electrode 218 of the pixel TFT is connected to the pixel electrode 300 made of ITO.

Finally, an annealing in a hydrogen atmosphere of 1 atm is carried out at 350° C. for 30 minutes in order to complete a pixel circuit of an active matrix circuit having TFTs.

As a modification of the second example, it is advantageous to arrange the TFTs of the pixel region shown in FIG. 5F in such a manner that the direction of crystal growth is approximately orthogonal to the direction of the carrier flow of the TFT. Thereby, it is possible to minimize an OFF current when the TFT is in its OFF condition because the carriers must pass across grain boundaries. On the other hand, the TFTs of a peripheral circuit shown in FIG. 4F are arranged so that the direction of the carrier flow is aligned with the direction of the crystal growth. Accordingly, the carriers flow along grain boundaries and it is possible to increase the mobility. In order to achieve such a configuration, during the manufacture of the pixel TFTs shown in FIGS. 5A-5F, nickel should be introduced into a region of the silicon film, which is in front of the TFT or behind the TFT in the drawing sheet. By doing so, the crystals laterally grow in a direction which is perpendicular to the direction along source and drain regions 212 and 213, resulting in that the carriers pass across grain boundaries. Other manufacturing conditions may be entirely the same as those explained before.

EXAMPLE 3

The present example is directed to a manufacture of an active matrix liquid crystal device as shown in FIG. 1. In the device of the present example, the TFTs of the pixel region are formed with a crystalline silicon film in which crystals grew in a direction perpendicular to the substrate surface while the TFTs of the peripheral circuit (also called as driver TFTs) are formed with a crystalline silicon film in which crystals grew in a direction parallel with the substrate surface. Therefore, the present example is characterized in that crystal growths of the pixel TFTs and the driver TFTs occur in different ways from each other.

The silicon film for forming the pixel TFTs will be directly added in its hole area with a catalyst material for promoting a crystallization thereof and then thermally crystallized.

Also, the silicon film for forming the driver TFTs will be crystallized by introducing a catalyst into a first region and then thermally annealed in order that the crystals grow from the first region toward a second region adjacent thereto horizontally with respect to the substrate.

In accordance with the present example, the amount of the catalyst element introduced into the foregoing regions is varied in each region. This is because the crystal structure of the obtained film depends upon the amount of the catalyst element. However, the concentration of the catalyst element in the active regions can be mad almost the same because the concentration of the catalyst element in the lateral growth region is smaller than that in the region to which the catalyst element is directly introduced.

FIGS. 6A-6F are cross sectional views for showing a manufacturing method of a TFT in the pixel region of FIG. 1 in accordance with the present example, while FIGS. 7A-7F are cross sectional views for showing a manufacturing method of a TFT in the peripheral circuit regions of FIG. 1 in accordance with the present example. Therefore, FIGS. 6A-6F and FIGS. 7A-7F correspond with each other and the both TFTs are formed on the same substrate.

Figure 6A:
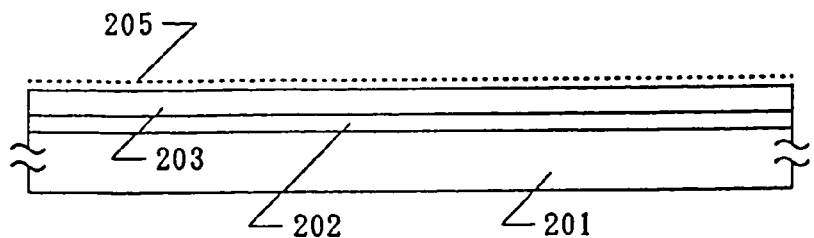
FIGS. 6A-6F show a manufacturing method of a thin film transistor for a pixel region in accordance with Example 3 of the present invention.
Figure 7A:
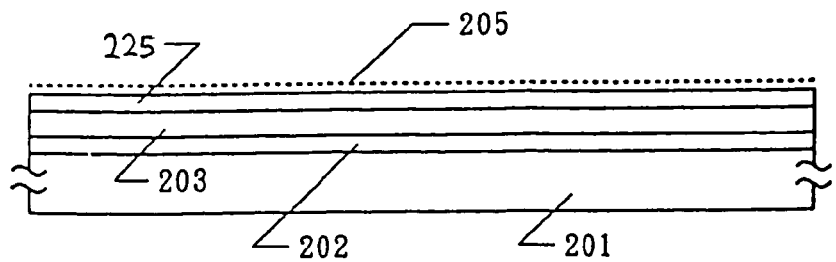
FIGS. 7A-7F show a manufacturing method of a thin film transistor for a peripheral circuit in accordance with Example 3 of the present invention.

Referring to FIGS. 6A and 7A, a surface of a substrate 201 is cleaned by a proper cleaning method and a silicon oxide film 202 is formed on the cleaned surface to a thickness of 2000 Å by plasma CVD using TEOS and oxygen as starting gases. Then, an intrinsic (i-type) amorphous silicon film 203 is formed by plasma CVD or LPCVD to a thickness of 500-1500 Å, for example, 1000 Å. Subsequently, a silicon oxide film 225 is formed by plasma CVD to a thickness of 500-2000 Å, for example, 1000 Å. The oxide film 225 is selectively etched in order that only the pixel region of the amorphous silicon film 203 is exposed. Therefore, the peripheral circuit region of the silicon film remains covered with the oxide film 225 which functions as a mask in the later step.

Then, an extremely thin oxide film (e.g. several tens Å thick) is formed on the exposed surface of the amorphous silicon film 203. This extremely thin oxide film improves the wetting property of the surface with respect to a solution which will be applied later. The oxide film may be formed by thermal oxidation, or a UV irradiation in an oxygen gas.

Thereafter, an acetic acid salt solution 205 which contain nickel is applied onto the entire surface by coating in order that the exposed surfaces of the amorphous silicon film are provided with nickel. The volume concentration of nickel in the acetate solution is 10 ppm.

After the coating, the substrate is heat treated at 200-500° C., for example, 300° C. so that nickel silicide is formed on the surface of the amorphous silicon film which is directly provided with the acetic acid salt solution. Accordingly, only the pixel region of the silicon film is provided with the nickel silicide while the peripheral circuit region of the silicon film is not provided with nickel silicide because of the existence of the mask made of the silicon oxide film 225.

Figure 7B:
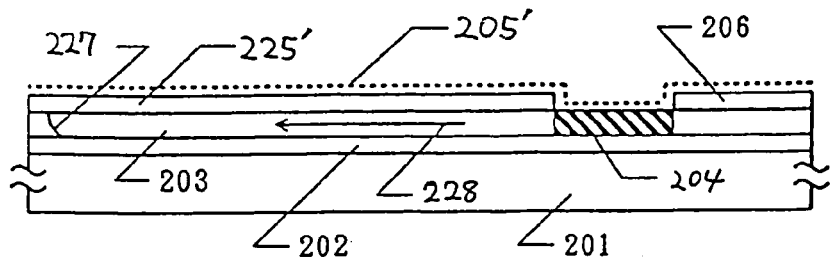

Then, referring to FIG. 7B, the silicon oxide film 225 used as a mask is removed and another silicon oxide film 225' is formed on the entire surface. The formation of the silicon oxide film may be done in the same manner as the formation of the oxide film 225. The silicon oxide film 225' is patterned to expose only a portion of the silicon film as shown in FIG. 7B. On the other hand, the silicon film 203 on the pixel region is completely covered with the silicon oxide film 225'.

In the above condition, an acetic acid salt solution 205' which contains nickel as a crystallization promoting catalyst is coated onto the entire surface. Therefore, only the exposed region of the silicon film is provided with the nickel. The volume concentration of the nickel in the solution is 100 ppm. Accordingly, the amount of nickel added to the silicon film is 10 times as high as the amount of nickel added to the silicon film in the former step as shown in FIG. 6A.

Thereafter, the substrate is heat treated at 200-500° C., for example, 300° C. in order to form nickel silicide on the exposed region 204 of the silicon film in FIG. 7B.

By the foregoing steps, the peripheral circuit region of the amorphous silicon film is provided with nickel at a concentration 10 times as high as the region of the amorphous silicon film in the pixel region.

The silicon film 203 provided with the catalyst for promoting the crystallization thereof is then crystallized by thermal annealing in a nitrogen gas at 500-620° C. for example at 550° C. for 4 hours. The crystallization proceeds in a different manner in the pixel region and the peripheral circuit region. That is, in the pixel region of the silicon film as shown in FIG. 6A, the crystal growth occurs perpendicularly to the substrate because the entire surface of the silicon film is provided with nickel. On the other hand, in the peripheral circuit region as shown in FIG. 7B, since the region 204 is selectively provided with nickel, the crystallization proceeds from the region 204 to a region 228 adjacent thereto in a lateral direction. The crystallization of the former type is called a vertical growth and the latter is called a lateral growth as said before.

The length of the lateral growth is about 30 µm. This can be increased by increasing the amount of the added nickel, by elevating the temperature of the thermal annealing and/or by increasing the time of the thermal annealing. Also, it was confirmed that the lateral crystal growth direction in the region 228 is aligned with the <111> axis of the crystal.

Figure 6B:
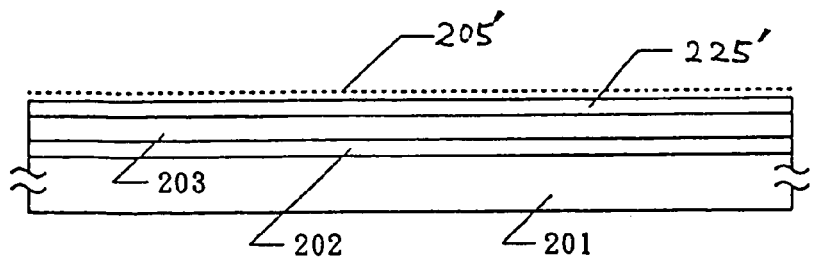

The concentration of nickel in the silicon film is $1 \times 10^{18}$ atoms/cm$^3$ at the pixel region of FIG. 6B, and $1 \times 10^{19}$ atoms/cm$^3$ at the region 204 of FIG. 7B, and $1 \times 10^{18}$ atoms/cm$^3$ at the region 228. Accordingly, the nickel concentration in active regions of TFTs for both of the peripheral circuit region and the pixel region is controlled to be $1 \times 10^{18}$ atoms/cm$^3$. Of course, it is possible to control the nickel concentration by changing the amount of nickel to be added. For example, when the crystallinity of the semiconductor film in the pixel region may be lowered, the nickel concentration in the solution 205 may be lowered. Also, when it is desired to increase the crystal growth length in FIG. 7B, the nickel concentration in the acetic acid salt solution 205' should be increased.

It is desirable to irradiate the semiconductor film with intense light for improving the crystallinity after the above crystallization. An infrared light having a wavelength of 1.2 µm or laser light may be used as a light source. Also, it is appropriate to irradiate only the peripheral circuit region with light in the same manner as in the first example of the present invention.

Figure 6C:
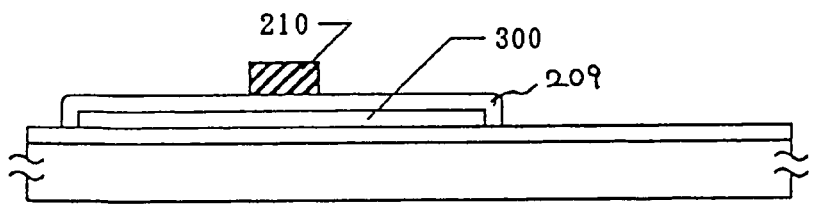

After the crystallization step, the silicon oxide film 225' is removed by etching and then the silicon film 203 is patterned by dry etching in order to form active regions 300 and 301 in the form of an island. In FIG. 6C, the active region 300 comprises the crystalline silicon in which crystals grew in a direction vertical to the substrate. Also, in FIG. 7C, the active region 301 comprises the crystalline silicon film in which crystals grew from the region 204 in a lateral direction.

The region 204 was directly introduced with nickel so that the concentration of the nickel in this region is higher. Also, the region 227 which is a top end of crystal growth also contains nickel at a higher concentration. Accordingly, the patterning of the silicon film is performed in such a manner that the active region does not overlap with the high concentration regions 204 and 227.

Figure 7C:
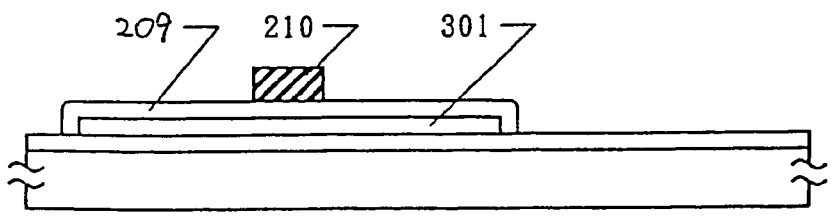

After the patterning, a silicon oxide film 209 of 1000 Å thick is formed by LPCVD as a gate insulating film. Subsequently, an aluminum film containing scandium 0.01 to 0.2% is deposited to 3000-8000 Å thick, for example, 6000 Å thick by sputtering, and then patterned into a gate electrode 210. (FIGS. 6C and 7C)

Figure 6D:
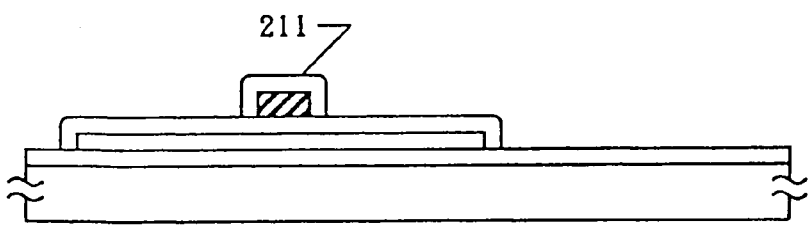
Figure 7D:
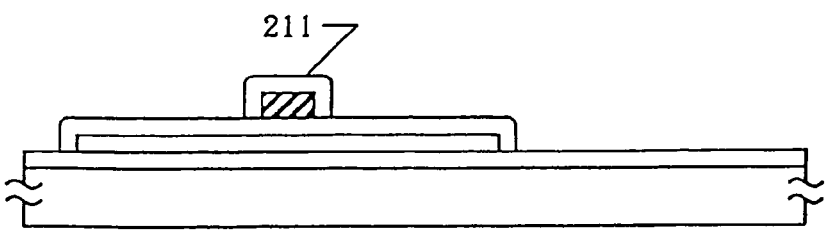

Then, referring to FIGS. 6D and 7D, the surface of the aluminum gate electrode is anodic oxidized to form an anodic oxide layer 211 of a thickness of 2000 Å. The anodic oxidation is carried out within an ethylene glycol solution in which a tartaric acid is contained at 1-5%. The thickness of the anodic oxide layer 211 will determine the thickness of the offset gate area in the subsequent impurity introducing step by ion doping.

Figure 6E:
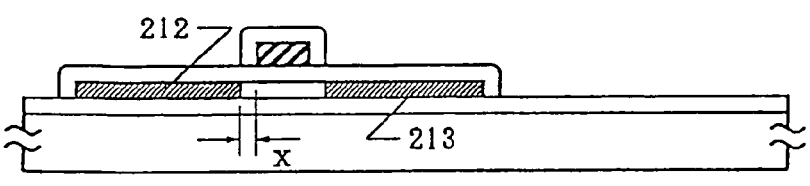
Figure 7E:
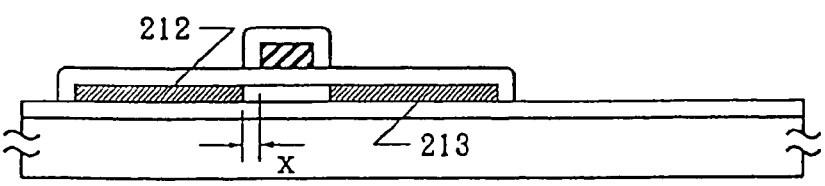

Referring then to FIGS. 6E and 7E, using the gate electrode 210 and the surrounding anodic oxide film 211 as a mask, an N-type conductivity impurity (phosphorous, for example) is introduced into the active layer in a self-aligning manner by ion doping method in order to form impurity regions 212 and 213 as source and drain regions. Phosphine ($PH_3$) is used as a dopant gas. The acceleration voltage is 60-90 kV, for example, 80 kV. The dose amount is $1 \times 10^{15}$-$8 \times 10^{15}$ $cm^{-2}$, for example, $4 \times 10^{15}$ $cm^{-2}$. As can be seen in the drawing, the impurity regions 212 and 213 are offset from the gate electrode by a distance "x". This configuration is advantageous for reducing a leak current (off current) which occurs when applying a reverse bias voltage (i.e. a negative voltage in the case of an NTFT) to the gate electrode. In particular, it is advantageous to provide an offset region in the TFT for the pixel region in order to prevent charges applied to a pixel electrode from leaking.

Also, when forming a CMOS structure for the peripheral circuit, it is necessary to introduce a P-type impurity as a dopant. In such a case, a mask may be used so that the ion doping can be selectively performed.

Thereafter, an annealing is performed with a laser irradiation. As a laser, a KrF excimer laser (wavelength: 248 nm, pulse width: 20 nsec.) or other lasers may be used. The conditions of the laser irradiation in the case of KrF excimer laser are: energy density is 200-400 $mJ/cm^2$, for example, 250 $mJ/cm^2$, a number of shots is 2-10 shots per one site, for example, 2 shots. Preferably, the substrate is heated to 200-450° C. to enhance the effect of the irradiation.

Figure 6F:
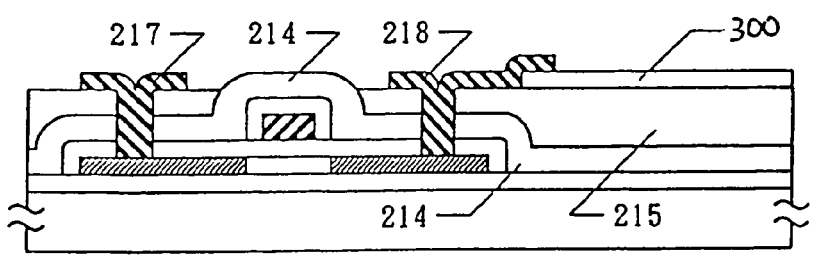
Figure 7F:
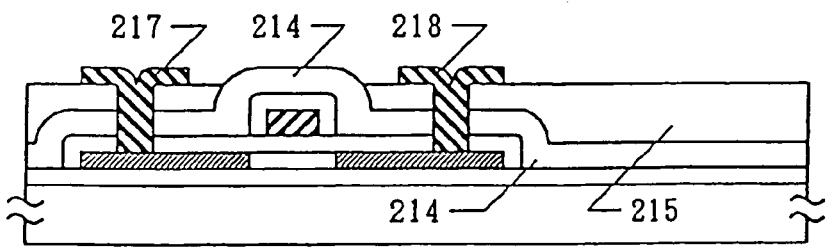

Referring to FIGS. 6F and 7F, an interlayer insulating film 214 of silicon oxide is formed through a plasma CVD to a thickness of 6000 Å. Further, a transparent polyimide film 215 is formed by spin coating to obtain a leveled surface. Then, a transparent conductive film made of, for example, indium tin oxide is formed on the leveled surface and patterned into a pixel electrode 300 as shown in FIG. 6F.

Then, the interlayer insulating films 214 and 215 are provided with contact holes, through which electrode/wirings 217 and 218 are formed to contact the impurity regions of the TFT. The electrode/wirings 217 and 218 are formed of a metallic material, for example, a multi-layer of titanium nitride and aluminum. As shown in FIG. 6F, one electrode 218 of the pixel TFT is connected to the pixel electrode 300 made of ITO.

Finally, an annealing in a hydrogen atmosphere of 1 atm is carried out at 350° C. for 30 minutes in order to complete the TFTs for the active matrix and the peripheral circuit of a liquid crystal device.

The TFT shown in FIG. 6F utilizes the vertical growth silicon film so that the carriers must pass across grain boundaries. Therefore, the mobility and the ON current is relatively small because of the influence of the grain boundaries. However, the OFF current can be reduced.

Also, the TFT shown in FIG. 7F utilizes the lateral growth silicon film so that carriers flow in a direction approximately parallel with the crystal growth direction. Therefore, the influence of the grain boundaries can be reduced and the ON current is increased.

EXAMPLE 4

In this example, an integrated circuit is to be formed on one glass substrate by mounting thereon a display, CPU, memory etc by employing the third aspect of the invention in which a desired crystalline structure or crystal structure (lateral growth or vertical growth) may be obtained in a desired region.

Figure 8:
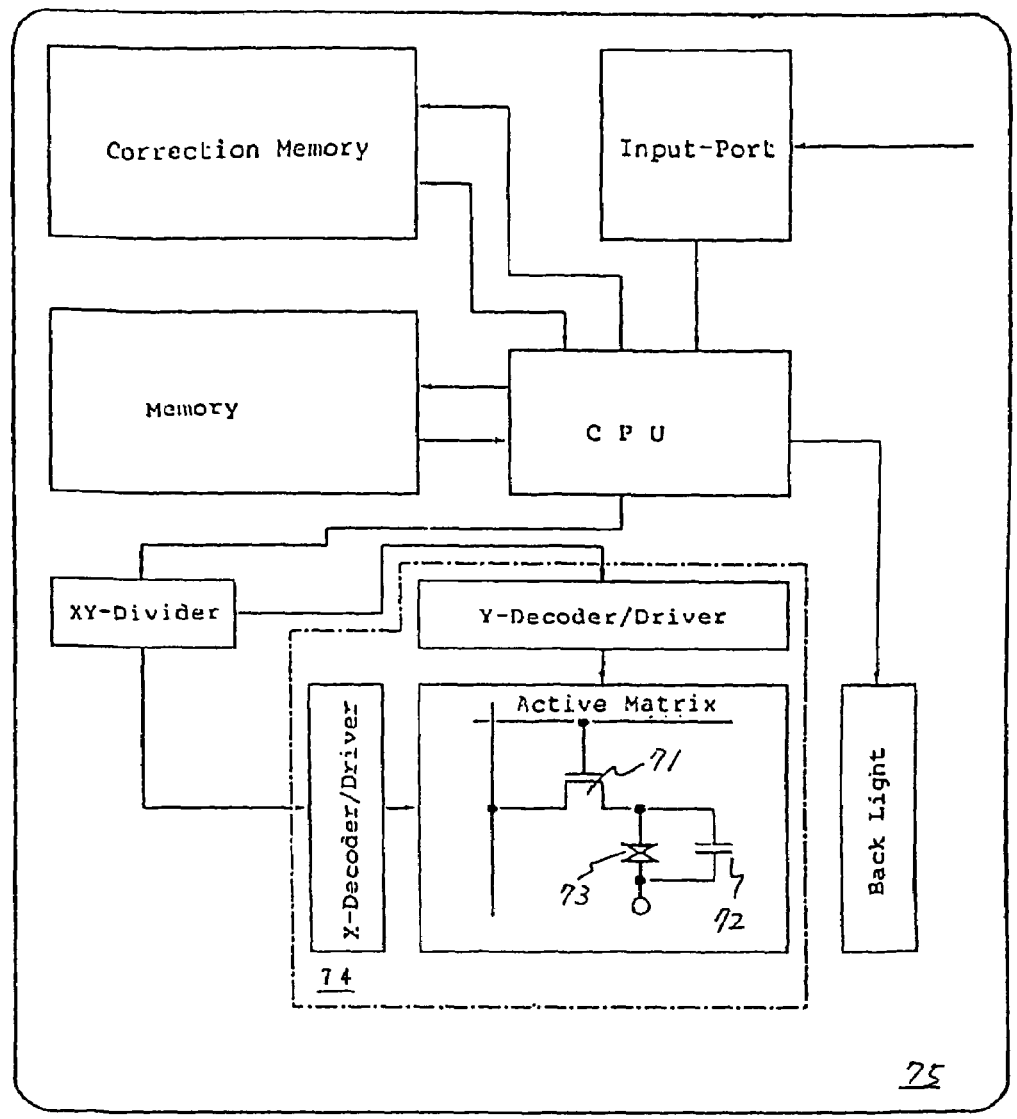
FIG. 8 shows a block diagram of an active matrix type liquid crystal device in accordance with Example 4 of the present invention.

FIG. 8 shows a block diagram of an electro-optical system (device). In the diagram, the input port is to read a signal input from an outside and to convert it into a display signal, and the correction memory is peculiar to each panel, which corrects the input signal or the like in accordance with a specific characteristics of an active matrix panel. In particular, the correction memory uses a non-volatile memory in which an information of each pixel is stored in order to perform the correction at each pixel. That is, if there is a defective pixel (point defect) in the electro-optical device, pixels surrounding the defective pixel are supplied with signals which are corrected in order to disappear or cover the defect pixel. Also, when there is a pixel of which brightness is lower than others, the signal to be applied to that pixel is corrected to be a larger signal, thereby, the brightness of that pixel becomes the same as its surrounding pixels.

The CPU and the memory are equivalent to those used in a conventional computer. Especially, the memory uses a RAM in which an image memory corresponding to each pixel is stored. Also, it has a function of changing an intensity of back light on the rear side of the substrate in response to the image information.

The reference numeral 74 shows a region on which a decoder/driver circuit which is a peripheral circuit is formed. 71 shows an active matrix TFT, 72 shows a capacitor, and 73 shows a liquid crystal. In this example, the foregoing circuits are formed on one substrate. And, a crystalline silicon film is selectively formed depending upon the required crystallinity or crystal structure.

While various examples have been disclosed, it is to be understood that the scope of the present invention should not be limited to those particular examples. Many modifications may be made without departing the scope of the invention. For example, while thin film transistors are mainly discussed, it is possible to form other types of a semiconductor device in accordance with the present invention, for example, a diode, photoelectric conversion device, etc. Also, the present invention is effective for the use of other catalyst materials in place of nickel. Furthermore, the catalyst may be first formed over a substrate and then a semiconductor film may be formed thereon.

What is claimed is:

1. A method of manufacturing a memory comprising the steps of:

depositing a semiconductor film comprising amorphous silicon over a substrate;

providing a portion of the semiconductor film comprising amorphous silicon with a metal containing material for promoting crystallization of the semiconductor film;

crystallizing the semiconductor film by heating wherein the crystallization proceeds in parallel with a surface of the substrate from the portion where the metal containing material is provided;

patterning the crystallized semiconductor film to form at least one semiconductor island wherein the crystals extend in parallel with the surface of the substrate through the semiconductor island;

forming an insulating film over the semiconductor island; and forming a gate electrode over the semiconductor island with the insulating film interposed therebetween.

2. The method according to claim 1 wherein said metal containing material comprises a metal selected from the group consisting of Ni, Pd, Pt, Cu, Ag, Au, In, Sn, P, As and Sb.

3. The method according to claim 1 further comprising a step of adding an impurity into the semiconductor island to form impurity regions with a channel region therebetween in the semiconductor island.

4. A method of manufacturing a memory comprising the steps of:

depositing a semiconductor film comprising amorphous silicon over a substrate;

applying a liquid to a surface of the semiconductor film wherein a metal containing material is contained in said liquid;

crystallizing the semiconductor film by heating wherein the metal diffuses through the semiconductor film during the crystallization;

patterning the crystallized semiconductor film to form at least one semiconductor island;

forming an insulating film over the semiconductor island; and forming a gate electrode over the semiconductor island with the insulating film interposed therebetween.

5. The method according to claim 4 wherein said metal containing material comprises a metal selected from the group consisting of Ni, Pd, Pt, Cu, Ag, Au, In, Sn, P, As and Sb.

6. The method according to claim 4 further comprising a step of adding an impurity into the semiconductor island to form impurity regions with a channel region therebetween in the semiconductor island.

7. A method of manufacturing a memory comprising the steps of:

depositing a semiconductor film comprising amorphous silicon over a substrate;

applying a liquid to a portion of the semiconductor film wherein a metal containing material is contained in said liquid;

crystallizing the semiconductor film by heating wherein the crystallization proceeds in parallel with a surface of the substrate from the portion of the semiconductor film;

patterning the crystallized semiconductor film to form at least one semiconductor island;

forming an insulating film over the semiconductor island; and forming a gate electrode over the semiconductor island with the insulating film interposed therebetween.

8. The method according to claim 7 wherein said metal containing material comprises a metal selected from the group consisting of Ni, Pd, Pt, Cu, Ag, Au, In, Sn, P, As and Sb.

9. The method according to claim 7 further comprising a step of adding an impurity into the semiconductor island to form impurity regions with a channel region therebetween in the semiconductor island.

10. A method of manufacturing a memory comprising the steps of:

depositing a semiconductor film comprising amorphous silicon over a substrate;

providing a portion of the semiconductor film comprising amorphous silicon with a metal containing material for promoting crystallization of the semiconductor film;

crystallizing the semiconductor film by heating wherein the crystallization proceeds in parallel with a surface of the substrate from the portion where the metal containing material is provided;

patterning the crystallized semiconductor film to form at least one semiconductor island forming an insulating film over the semiconductor island; and forming at least two impurity regions in the semiconductor island with a channel region therebetween, wherein crystals extend in the channel region along a carrier flow direction of the channel region.

11. The method according to claim 10 wherein said metal containing material comprises a metal selected from the group consisting of Ni, Pd, Pt, Cu, Ag, Au, In, Sn, P, As and Sb.

12. The method according to claim 10 further comprising a step of forming a gate electrode over the semiconductor island.

13. A method of manufacturing a memory comprising the steps of:

depositing a semiconductor film comprising amorphous silicon over a substrate;

applying a liquid to a portion of the semiconductor film wherein a metal containing material is contained in said liquid;

crystallizing the semiconductor film by heating wherein the crystallization proceeds in parallel with a surface of the substrate from the portion of the semiconductor film;

patterning the crystallized semiconductor film to form at least one semiconductor island;

forming an insulating film over the semiconductor island; and forming at least two impurity regions in the semiconductor island with a channel region therebetween, wherein crystals extend in the channel region along a carrier flow direction of the channel region.

14. The method according to claim 13 wherein said metal containing material comprises a metal selected from the group consisting of Ni, Pd, Pt, Cu, Ag, Au, In, Sn, P, As and Sb.

15. The method according to claim 13 further comprising a step of forming a gate electrode over the semiconductor island with the insulating film interposed therebetween.

16. The method according to claim 1 further comprising a step of irradiating the crystallized semiconductor film with a laser light prior to the patterning.

17. The method according to claim 4 further comprising a step of irradiating the crystallized semiconductor film with a laser light prior to the patterning.

18. The method according to claim 7 further comprising a step of irradiating the crystallized semiconductor film with a laser light prior to the patterning.

19. The method according to claim 10 further comprising a step of irradiating the crystallized semiconductor film with a laser light prior to the patterning.

20. The method according to claim 13 further comprising a step of irradiating the crystallized semiconductor film with a laser light prior to the patterning.

21. The method according to claim 1 wherein said memory includes a non-volatile memory.

22. The method according to claim 1 wherein said memory includes a RAM.

23. The method according to claim 4 wherein said memory includes a non-volatile memory.

24. The method according to claim 4 wherein said memory includes a RAM.

25. The method according to claim 7 wherein said memory includes a non-volatile memory.

26. The method according to claim 7 wherein said memory includes a RAM.

27. The method according to claim 10 wherein said memory includes a non-volatile memory.

28. The method according to claim 10 wherein said memory includes a RAM.

29. The method according to claim 13 wherein said memory includes a non-volatile memory.

30. The method according to claim 13 wherein said memory includes a RAM.

31. The method according to claim 4 wherein said metal containing material is dissolved in said liquid.

32. The method according to claim 7 wherein said metal containing material is dissolved in said liquid.

33. The method according to claim 13 wherein said metal containing material is dissolved in said liquid.

* * * * *